United States Patent [19]

Shaw

[11] 4,025,898
[45] May 24, 1977

[54] RECORDING REPRESENTATIONS OF DISRUPTED SPACE PATTERNS

[76] Inventor: Lew Shaw, 2955 Diamond Hill Road, Cumberland, R.I. 02864

[22] Filed: Jan. 9, 1976

[21] Appl. No.: 647,658

Related U.S. Application Data

[63] Continuation-in-part of Ser. No. 572,132, April 28, 1975.

[52] U.S. Cl. .................. 340/146.3 E; 250/237 G; 350/162 R; 356/71
[51] Int. Cl.² .................................... G06K 9/00
[58] Field of Search .............. 340/146.3 E; 356/71, 356/169, 156; 350/162 R, 162 SF, 316; 250/237 R, 237 G

[56] References Cited

UNITED STATES PATENTS

| | | | |
|---|---|---|---|
| 2,646,717 | 7/1953 | Selgin | 356/71 |
| 2,964,641 | 12/1960 | Selgin | 356/71 |
| 3,292,149 | 12/1966 | Bourne | 340/146.3 E |
| 3,510,223 | 5/1970 | Lohmann | 340/146.3 P |
| 3,511,571 | 5/1970 | Ogle | 356/71 |
| 3,599,147 | 8/1971 | Rogers et al. | 340/146.3 P |
| 3,604,806 | 9/1971 | Redman | 356/71 |
| 3,740,153 | 6/1973 | Wood | 356/71 |
| 3,759,618 | 9/1973 | Rogers et al. | 250/237 G |
| 3,876,304 | 4/1975 | Novak | 356/71 |

OTHER PUBLICATIONS

Marcus et al., "Moire Pattern Decoding," *IBM Tech. Disclosure Bulletin*, vol. 11, No. 5, Oct. 1968, pp. 541–542.

Primary Examiner—Leo H. Boudreau

[57] ABSTRACT

A method records the representations of disrupted space patterns such as fingerprints by generating phase frequency differences or moiré representations of the image of the patterns or fingerprints which are converted to a waveform of electrical signals which are stored with or without further processing.

7 Claims, 4 Drawing Figures

RECORDING REPRESENTATIONS OF DISRUPTED SPACE PATTERNS

CROSS REFERENCE TO RELATED APPLICATION

This application is a continuation-in-part of my copending application Ser. No. 572,132 filed Apr. 28, 1975.

BACKGROUND OF THE INVENTION

This invention pertains to the recording and processing of information about disrupted space patterns.

Disrupted space patterns take on many forms such as fingerprints, snout prints, pictures, printed currency or other printed matter. While each of these categories can require classification, the following discussion will be mainly concerned with fingerprints.

Each fingerprint is unique. It has been said that there are no two fingerprints which are alike, and in the history of fingerprint indentification, no evidence appears to have been found to dispute this contention. The enormity of the problem of classifying fingerprints, storing the data and then retrieving the information in order to identify an unknown print as a duplicate of the original has led to many methods currently in use or abandoned.

In all previous and current methods, various procedures are used to secure a fixed reference point or location for a fingerprint or some characteristic of a fingerprint, such as a delta formation, in order to compare subsequent prints which might have been made by use of the same finger pattern. In other words, an invariate matching is sought as a true or positive identification.

One problem of previous and current systems is the inherent nature of the classification system itself, i.e., experienced workers can assign different classifications to the same print where borderline definitions exist which describe the nature of the print design. Through assignment to sub-groups, the storing of information may be lost to another worker whose perception of the pattern causes him to assign it to yet another sub-group classification.

A serious drawback to present systems of fingerprinting is the difficulty of establishing a center in any fingerprint, of registering an exact position of any one print in order to compare other prints with it. It is estimated, furthermore, that at least 5% of all fingerprints do not have a delta formation thereby creating an insurmountable problem for any method, heretofore, of fingerprint classification and identification.

Furthermore, from a practical viewpoint, fingerprint taking itself varies to a very great extent because of inks, pressures of the print taken, the person taking the print, the cooperation or lack of cooperation of the person being fingerprinted, etc.

In essence, all known approaches rely on the concept of pattern recognition which assumes an original fixed referent to which an invariate copy is sought.

SUMMARY OF THE INVENTION

It is the general object of the invention to provide a method and means for recording disrupted space patterns such as fingerprints so that their classification, comparison and retrieval is simplified.

Briefly, the invention contemplates generating phase frequency difference representations of the patterns and converting the representations to electrical signals which are then stored.

Other objects, the features and advantages of the invention will be apparent from the following detailed description when read with the accompanying drawing which shows apparatus for performing the invention. In the drawing:

DESCRIPTION OF THE PREFERRED EMBODIMENTS

Before describing the apparatus for practicing the invention, the basic fundamentals utilized by the invention will be discussed. It is well known that the superposition or interference of two periodic structures results in an optical image having frequency phase differences or beats. The most common name for this phenomenon is moire or moire patterns. Since fingerprints are a periodic line pattern one need only have another periodic structure to create the moire pattern.

Figure 1:
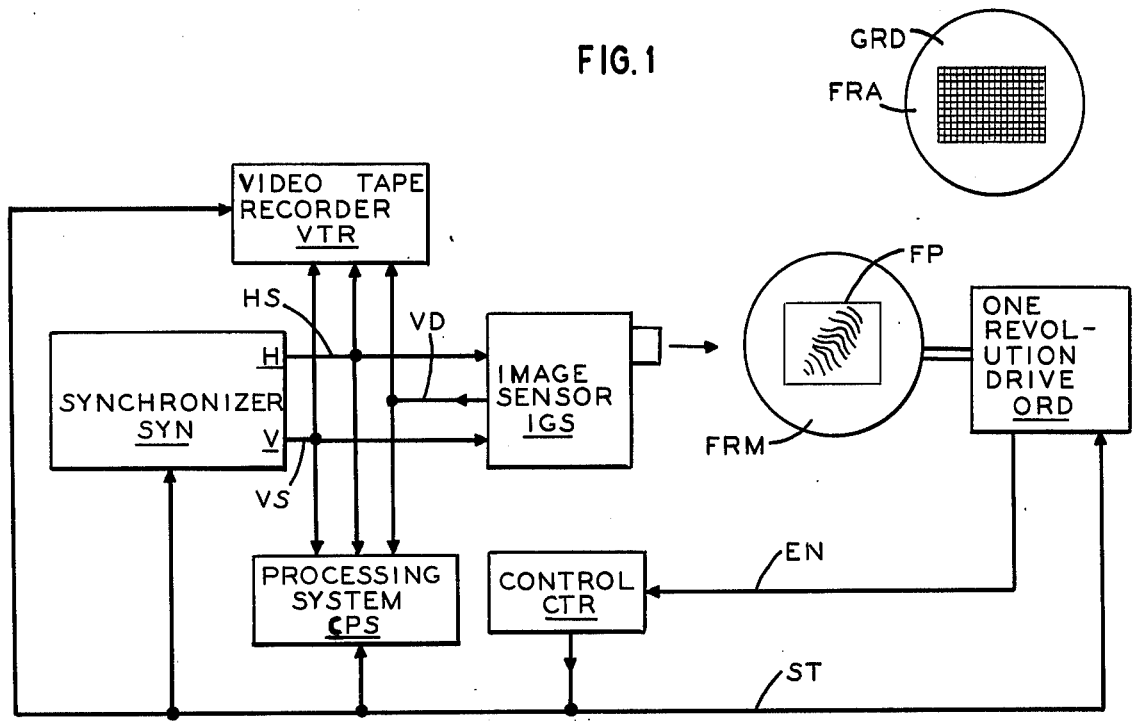
FIG. 1 is a block diagram for a first embodiment of the invention.

In FIG. 1 the second periodic structure is conveniently provided by the target grid of an image sensor IGS in the form of an image orthicon tube. More particularly, a card FP carrying the image of a fingerprint to be recorded is mounted in a frame FRM which can be driven through one cycle of revolution by a one revolution drive ORD. The frame FRM is located a given distance from an image sensor IGS whose lens is focussed on card FP. Video signals from the image sensor IGS are fed via line VD to a video tape recorder VTR and a processing system CPS. The video tape recorder VTR, image sensor IGS and processing system CPS are all synchronized for a conventional parallel line raster scan by horizontal synchronizing signals and vertical synchronizing signals on lines HS and VS respectively, from synchronizer SYN.

In order to record the representation of a fingerprint one mounts the card FP in frame FRM and then operates control CTR in the form of a switch which feeds a signal on line ST to one revolution drive ORD, processing system CPS, synchronizer SYN and video tape recorder VTR. Drive ORD in response thereto causes the frame FRM to rotate about an axis perpendicular to the image plane of the card FP. At the same time synchronizer SYN begins transmitting the horizontal and vertical synchronizing pulses to cause image sensor IGS to perform the raster scans. Also the signal alerts video tape recorder VTR to record the recieved video signals and the processing system CPS to periodically sample the video signals, and convert them to binary signals for processing and storage. At the end of the revolution, drive ORD transmits a signal on line EN to control CTR to terminate the signal on line ST. With the disappearance of the signal on line ST the system returns to a rest state.

The video tape recorder VTR can be a conventional video tape recording device having external horizontal and vertical sync inputs. Similarly the image sensor has external horizontal and vertical sync inputs. The synchronizer SYN can be one free running pulse generator which periodically emits pulses on line VS and another pulse generator which emits pulses on line HS at a frequency which is say 1/1000 of the pulses on line VS. The control CTR can merely be a flip-flop whose set input is connected to a manually operated switch, whose reset input is connected to line EN and whose output is connected to line ST. One revolution drive ORD can be a motor drive and motor responsive to the signal on line ST. In addition a fiducial transducer on the shaft can generate the signal on line EN when the shaft has a particular position.

The processing system CPS can have an analog-to-digital encoder for receiving the video signals on line VD and converting them to binary numbers. The encoder can be periodically sampled and the numbers present during the sampling stored as a representation of the fingerprint. Thus the processing system will store in a memory a number unique to the fingerprint while the video tape recorder VTR stores a different representation of the fingerprint, i.e., the pictures of the varying moire pattern. Note both the stored number and the picture are unique to the fingerprint. At a later time one can locate the fingerprint by entering the number into the system. This can be accomplished by mounting an unknown fingerprint onto the frame and going through the above described routine to generate a number in the computer, and then searching the memory for that same number. Upon match, the processing system can print out information about the owner of the fingerprint which had been previously recorded with the number. In addition, the processing system can instruct the video tape recorder to play back the pictures associated with the located fingerprint information.

If one does not wish to rely on the periodic structure of the image orthicon, or if an image sensor IGS not having a periodic structure is used, one may interpose between the sensor IGS and the frame FRM another frame FRA having a grid structure GRD, an array of two orthogonal sets of parallel lines with a spacing in the order of the spacing normally found in fingerprints.

Figure 2:
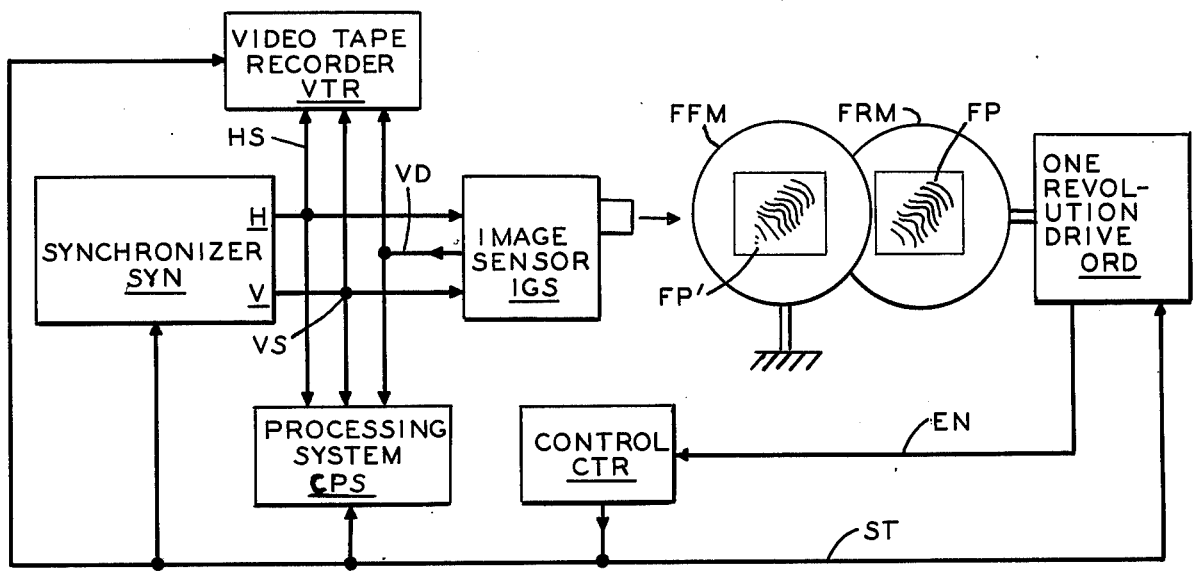
FIG. 2 is a block diagram of a second embodiment of the invention.

The system of FIG. 2 is the same in all respects to the system of FIG. 1 except for the means for generating the moire patterns and the image sensor IGS. In particular, the frame FRM supports an image FP of the fingerprint and another fingerprint mounted on a fixed frame FFM located between rotatable frame FRM and the image sensor IGS.

The image sensor IGS can be a color television camera without a periodic structure. Now two possibilities are available. The fingerprint image in frame FRM can be a black and white positive while the fingerprint image in the fixed frame FFM can be a black and white negative of the same fingerprint. Or, the fingerprint image in the rotatable frame FRM can be a green print while the fingerprint image in the fixed frame FFM can be a red print or vice versa. In either case the prints in the frames are initially aligned to exact superposition so that there is a null phase difference. The print in frame FRM is rotated for a complete 360° cycle as described for FIG. 1 with the same results.

Note for the systems described for both FIGS. 1 and 2 a standard distance would be set between the image sensor lens and the fingerprint card for all prints. Even if the individual print is not exactly in the center of the scanning field all the information of the phase differences will be recorded. The information might appear more toward the right or left of center but all the information is present and none of the information is lost or changed by such shifts or because of non-centering.

If one does not wish to use the technique of rotating the fingerprint image it is still possible to generate the patterns by varying the axial position between the lens of the image sensor IGS and the frame FRM. For each distance between these two elements there will be a different moire pattern. This technique does not rely on xy co-ordinates as with conventional pattern recognition for the location of the same referent. While the image sensor IGS has been described as being an image orthicon or a color television camera, other devices such as image dissectors can be used. In addition, part of the conversions from analog signals to specific digital numbers can be performed by such devices as the Optical Data Digitizers available from EMR Photoelectric of Princeton N.J. 08540.

Figure 3:
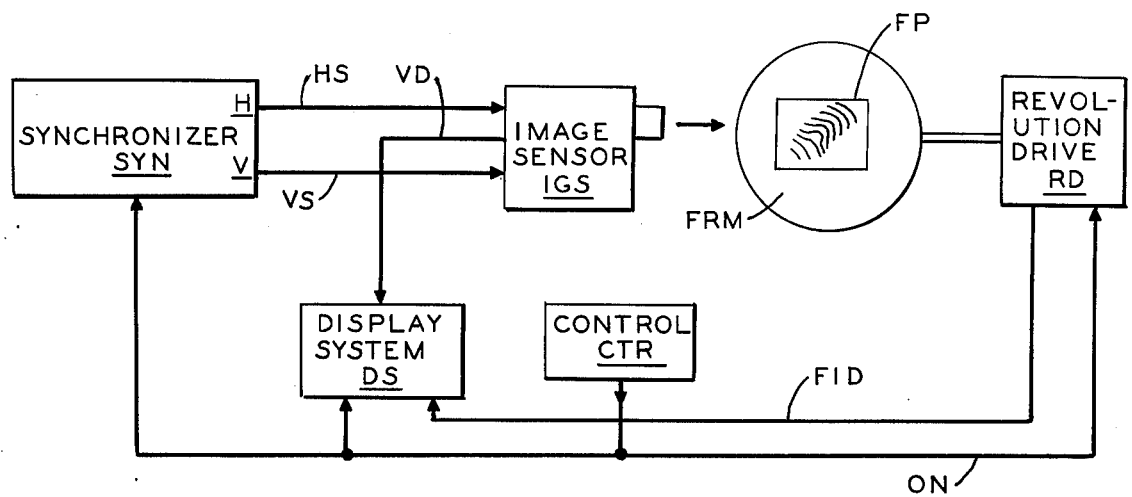
FIG. 3 is a block diagram of a further embodiment of the invention.

In FIG. 3 there is shown another embodiment of the invention. In particular the card FP carrying the image of a fingerprint to be recorded is again mounted in frame FRM which can be driven through cycles of revolution by a revolution drive RD. The frame FRM is located a given distance from an image sensor IGS whose lens is focussed on card FP. Video signals from the image sensor IGS are fed via line VD to the display system DS. The image sensor IGS is synchronized for a conventional parallel line raster scan by horizontal synchronizing signals and vertical synchronizing signals on lines HS and VS respectively, from synchronizer SYN.

In order to record the representation of a fingerprint one mounts the card FP in frame FRM and then operates control CTR in the form of a switch which feeds a signal on line ST to energize revolution drive RD, display system DS and synchronizer SYN. Drive RD in response thereto causes the frame FRM to rotate about an axis perpendicular to the image plane of the card FP. At the same time synchronizer SYN begins transmitting the horizontal and vertical synchronizing pulses to cause image sensor IGS to perform the raster scans. Also the signal alerts the display system DS to accept the video signals, and display them for processing and storage. Once per revolution, drive RD transmits a signal on line FID to display system DS to trigger the next sweep of the display.

Figure 4:
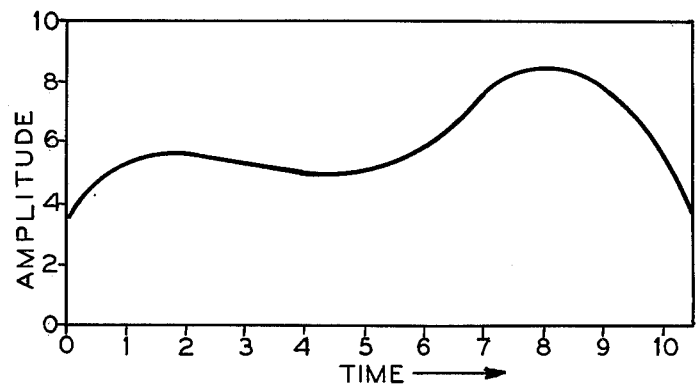
FIG. 4 is a charge used in explaining the embodiment of FIG. 3.

The display system DS displays a trace similar to that shown in FIG. 4 which is characteristic of the fingerprint for one revolution thereof. In fact the two dimension picture of the fingerprint is converted to a single curve. In other words the curve or waveform is the representation of the fingerprint. This waveform can be converted to digital information in the following manner. The screen of the display is provided with a coordinate system as shown. For each time increment, the amplitude of the curve is read off. For example, for time increment 1 the amplitude is 6, In this way the ten digit number 6665668986 can be constructed. This number which is unique to that fingerprint can be stored on a card with the information about the owner. Later, when an unknown print is processed in the same manner to obtain its characteristic number, that number can then be looked up in the file of all stored numbers to identify the owner. A suitable display system can be the Tektronix Type RM529 Waveform Monitor which is a self contained cathode ray oscilloscope specifically designed for video-waveform monitoring at television transmitters and studio facilities. The monitor is obtainable from Tektronix, Inc., Beaverton, Oreg. 97005.

The display system DS of FIG. 3 can also be a fast fourier transform analyzer. Such an analyzer is the Digital Fourier Signal Analyzer Model 5451B of Hewlett Packard, Palo Alto, Calif. 94304. This device performs the analysis on the waveform and converts the analysis to a series of digit numbers which can be stored in the mass storage of the system for later retrieval to perform cross correlations with other waveforms which represent other fingerprints.

Another possibility is the use of an analog-to-digital converter feeding a PDP-8 Computer of Digital Equipment Corporation, Maynard, Mass. 01754 which has been programmed with its Auto and Cross-Correlation Package.

A highly important advantage of this invention is the ability to search a data bank for the matching key number of a latent or single fingerprint which needs to be indentified. Until now, it has been necessary to have or make a complete set of all ten fingerprints of the individual before a search for a match could be attempted. Any single print can be classified according to the invention by creating and recording phase frequency differences and the key number of this classification can be run through a processor to find whether this key number is on file from previously stored data.

What is claimed is:

1. The method of recording a representation of a fingerprint comprising the steps of rotating through at least one complete rotation, a planar image of the fingerprint about an axis perpendicular to the planar image, generating Moiré patterns of the planar image of the fingerprint during rotation, converting the Moiré patterns to electrical signals, and storing representations of the electrical signals.

2. The method of claim 1 wherein the generating step comprises scanning the image of the pattern with a raster composed of a set of parallel lines.

3. The method of claim 1 wherein the generating step comprises optically superimposing another identical image of the fingerprint onto the image of the fingerprint and mutually rotating the images about an axis substantially perpendicular to their planes.

4. The method of claim 1 wherein the generating step comprises optically superimposing a planar array of regularly spaced lines on the image and mutually rotating the planar array and image about an axis substantially perpendicular to their planes.

5. The method of claim 1 wherein the representations of the electrical signals are digital values.

6. The method of claim 1 wherein the converting step includes a Fourier transformation on the electrical signals.

7. Apparatus for recording a representation of a fingerprint comprising supporting means for supporting the optical image of a fingerprint, a raster-driven image orthicon device aimed at the optical image of the fingerprint for generating electrical signals representing Moiré patterns of the fingerprint, means for rotating the supporting means and the optical image of the fingerprint through at least 360° about an axis parallel to the optical axis of the image orthicon device, and storing means for storing representations of the electrical signals generated by the image orthicon device while the optical image of the fingerprint is rotated through 360°.

* * * * *